United States Patent [19]
Tyson

[11] Patent Number: 5,705,216
[45] Date of Patent: Jan. 6, 1998

[54] PRODUCTION OF HYDROPHOBIC FIBERS

[76] Inventor: George J. Tyson, 259 Finestra Dr., Henderson, Nev. 89014

[21] Appl. No.: 514,263

[22] Filed: Aug. 11, 1995

[51] Int. Cl.⁶ .................................................. A23K 1/00
[52] U.S. Cl. .................. 426/478; 426/443; 426/615; 426/635; 426/807; 162/91; 162/96; 162/97; 162/99; 127/37
[58] Field of Search .................... 426/478, 807, 426/516, 31, 271, 443, 615, 635; 127/37; 162/14, 90, 99, 91, 96, 97

[56] References Cited

U.S. PATENT DOCUMENTS

| | | |
|---|---|---|
| 4,136,207 | 1/1979 | Bender . |
| 4,187,141 | 2/1980 | Ahrel . |
| 4,214,947 | 7/1980 | Berger . |
| 4,270,976 | 6/1981 | Sandstrom et al. ............ 162/26 |
| 4,298,425 | 11/1981 | Ranzen et al. . |
| 4,311,553 | 1/1982 | Akerlund et al. . |
| 4,372,812 | 2/1983 | Phillips et al. . |
| 4,444,621 | 4/1984 | Lindhal . |
| 4,451,332 | 5/1984 | Annergren et al. . |
| 4,459,174 | 7/1984 | Papageorges et al. . |
| 4,649,113 | 3/1987 | Gould . |
| 4,842,877 | 6/1989 | Tyson . |
| 5,023,097 | 6/1991 | Tyson . |
| 5,503,709 | 4/1996 | Burton ............................ 162/6 |

*Primary Examiner*—Anthony J. Weier
*Attorney, Agent, or Firm*—DeWitt Ross & Stevens SC

[57] ABSTRACT

A woody or non-woody biomass is delignified through continuous extrusion technology, utilizing high-pressure steam to break down complex biomass materials. The process is useful to form a hydrophobic fiber material for use as an extrusion filler, a plastics modifier, and in the papermaking arts. Alternatively, the process is useful for preparing dietary feeds for ruminant animals, as well as to produce a broad range of alcohols or polymers from lignocellulosic substrates.

12 Claims, 2 Drawing Sheets

PRODUCTION OF HYDROPHOBIC FIBERS

FIELD OF THE INVENTION

The present invention relates to the production of hydrophobic cellulose-based materials from biomass. More specifically, the present invention relates to a method for producing hydrophobic cellulose-containing fibers which can be used in a variety of end uses, including dietary fiber, plastic fillers and modifiers, and paper pulp.

DESCRIPTION OF THE PRIOR ART

The importance of dietary fiber for consumption in both humans and non-human mammals cannot be overemphasized. Dietary fiber plays a major role in health and disease resistance, physiological metabolism, and in preventative medicine. There has been considerable effort on the part of food manufacturers to develop fiber-rich foods in order that human consumers may more easily benefit from the advantages of dietary fiber.

Further, many high-fiber plant materials can be used as a source of carbohydrates for ruminant feeds. However, in order to benefit from these advantages, the lignocellulosic materials in the plant residues must be converted into materials which can be readily metabolized. Specifically, the polysaccharide portion of these agricultural residues must be converted into monomeric sugars.

In order to accomplish this, it is important to break down the lignins in the plant residue to release the beneficial polysaccharides in the plant cell wall.

Additionally, as has been known since early experiments using cellulose-based materials, physical and chemical modification of the linkages between the lignin and the cellulose in lignocellulosic biomass may result in significant alteration of the physical properties of the biomass starting material. These modifications have been utilized in the past to manufacture materials having interesting characteristics, for instance, cellophane.

As is generally known in the art, lignins are complex natural polymeric products that occur together with cellulose, normally in the woody part of plants such as trees and shrubs. Because lignins are high molecular weight polymers, their exact structures as they occur in nature are unknown. It is known, however, that lignins are composed of three basic building blocks: coniferyl alcohol, sinapyl alcohol, and p-coumaryl alcohol. All three are propyl-substituted phenol derivatives. Different plant species apparently have lignins of different compositions. For instance, guaiacyl lignins are derived mainly from coniferyl alcohol, while guaiacyl-syringyl lignins contain both coniferyl alcohol and a significant amount of sinapyl alcohol. p-Coumaryl alcohol is a minor constituent (1–5%) of all lignins. In nature, the polymeric structures of the lignins are intimately bound by a variety of different linkages to the cellulosic units within the plant material. Dissociation of the lignin from the cellulose is a key step in the utilization of the cellulose for dietary and other purposes.

Originally, the delignification process used sulfuric acid and chlorine as the main reagents. However, due to environmental concerns regarding the use of chlorine, the sulfuric acid process is now being widely replaced with a process which uses sodium hydroxide and oxygen to effect delignification.

An example of delignification of woody fibers is described in U.S. Pat. No. 4,459,174, to Papageorges, et al. This reference discloses a process for the delignification and bleaching of chemical and semi-chemical cellulosic pulps by subjecting the pulp to a two-step treatment with oxygen followed by a subsequent treatment with peroxide.

U.S. Pat. No. 4,451,332, to Annergren, et al., is directed to a method for delignification of lignocellulose-containing fiber material comprising mixing an oxygen-containing gas with the cellulose fiber material in order to atomize the gas and form a foam of the gas and the cellulose fiber material. This process provides a bleached, delignified cellulose fiber without bleaching the lignin substance extracted from the material.

U.S. Pat. No. 4,372,812, to Phillips, et al. is directed to a chlorine-free bleaching process for lignocellulosic pulp. This process is characterized by a series of bleaching stages comprising in sequence a peroxide bleaching stage, and at least one ozone bleaching stage.

U.S. Pat. No. 4,311,553, to Akerlund, et al. is directed to a method of producing peroxide-bleached pulp by impregnating lignocellulosic fiber material with an aqueous silicate solution containing a sequestering agent. The fiber material is preheated with saturated steam and defibrillated between two grinding disks in an atmosphere of saturated steam at a temperature of between 100°–170° C.

U.S. Pat. No. 4,298,425, to Ranzen, et al. is directed to a method and apparatus for producing fiber pulp of improved paper-forming characteristics from lignocellulose-containing material such as wood chips and the like.

U.S. Pat. No. 4,214,947, to Berger is directed to the treatment of a cellulosic material in the form of wood chips to produce at least partial delignification without mechanical grinding. The material is brought into contact with a reagent, e.g., steam or a chemical reagent, and is subjected to alternate increases and decreases in pressure.

U.S. Pat. No. 4,187,141, to Ahrel is directed to a method of producing mechanical pulp of improved brightness and light-scattering properties from wood chips. The wood chips are ground between a pair of disks. The wood fibers are then impregnated with a solution of alkali and introduced into a pressure vessel which is in communication with the grinding zone.

U.S. Pat. No. 4,444,621, to Lindahl is directed to a process and apparatus for re-resination and brightness enhancement of cellulose pulp by adding an alkali to the pulp in combination with an oxidizing bleaching agent.

While the above processes are mainly directed to the delignification of woody-like materials, there are other processes known to the art which disclose the delignification of non-woody biomass to produce food fit for human and animal consumption. For example, U.S. Pat. No. 4,136,207, to Bender discloses a process for the delignification and fractionation of non-woody substrates via acid hydrolysis. In a first step, this process uses a pH of 1.5 with heat and pressure and a residence time of 6–13 minutes. Hemicellulose is extracted from the residues, and the residues are subjected to hydrolysis for further fermentation to ethanol, butanol, acetic acid, furfural, and xylitol. The cellulose and lignin are then treated with an alkaline solution and separated for independent uses.

U.S. Pat. No. 4,649,113, to Gould discloses a batch process for the delignification of agricultural residues to produce cattle feeds, chemical feeds, or dietary fibers. Agricultural crop residues and other non-woody lignocellulosic plant substrates are treated with hydrogen peroxide at a controlled pH within the range of about 11.2 to 11.8. The substrates are partially delignified thereby. This process does not use a reactor or a mechanical shear and compression device, but rather utilizes alkaline hydrogen peroxide solutions having a pH as described above. The cell walls are fractured in approximately 4 to 6 hours. The product can be used for animal feed. It is also possible to separate the liquid from the cell walls if a dietary fiber product is desired.

U.S. Pat. Nos. 4,842,877 and 5,023,097, both to Tyson, describe a process for delignifying non-woody biomass. In this process, various non-woody types of biomass are delignified by extruding the biomass under alkaline conditions in the presence of hydrogen peroxide. The process is limited in that it only functions with the addition of hydrogen peroxide, and can only be used to delignify non-woody biomass substrates. The process can be used to produce a nearly white, non-woody cellulosic fiber.

A Canadian company, Stake Technology, utilizes a modified version of steam explosion to delignify lignocellulosic material. In this process, lignocellulosic biomass is compressed into a dense plug. The plug is then digested with steam at a pressure of 800 pounds per square inch. The plug is then rapidly decompressed to atmospheric pressure. This causes explosive decompression which breaks the chemical bonds between the lignins and the cellulose of the biomass. The lignin can then be separated from the cellulose and hemicellulose within the lignocellulosic biomass.

While there are processes and apparatuses available which delignify both woody and non-woody cellulosic materials, these processes have inherent deficiencies. For example, with the process as disclosed in the '113 patent to Gould, maximum delignification of lignocellulosic materials is achieved by treatment with an aqueous solution of hydrogen peroxide at pH 11.4 for 4 to 6 hours at temperatures between approximately 50° and 120° F. In this process, a substantial mount of chemical reagents and time are utilized in order to effect the required delignification of the fiber.

The Tyson patents, above, describe a delignification process which, like Gould, utilizes a significant mount of hydrogen peroxide. Additionally, this process can only be used to delignify non-woody biomass substrates.

SUMMARY OF THE INVENTION

It is a principal aim and use of the present invention to provide a process for treating woody and non-woody lignocellulosic biomass to form a hydrophobic lignocellulosic product suitable for use as a plastic filler or modifier in such applications as extrusion and injection molding.

A further aim of the present invention is to provide a rapid and continuous delignification process which permits the efficient utilization of woody and non-woody agricultural residues.

It is also an aim of the present invention to provide a process for the delignification of waste or very low value agricultural biomass or industrial and post-consumer lignocellulosic waste to produce value-added foodstuffs such as natural sweeteners; solvents, fillers, and the like.

It is also an aim of the present invention to provide a nutritional ruminant feed source which is more economical than currently available feedstuffs.

It is another aim of the present invention to produce a broad range of feedstock chemicals, including ethanol, butadiene, acetic acid, lactic acid, and the like.

It must be noted that delignification of biomass is an important step in the efficient production of ethanol from biomass. Ethanol production from biomass offers a renewable source of liquid fuel which can be produced entirely within the borders of the United States. For many, such an energy source is seen as crucial to end our dependence upon foreign sources of petroleum. Due to economic reasons, however, ethanol is produced almost exclusively from maize. One of the aims of the present invention is to provide a method which allows the economical production of ethanol (and other chemicals) from any lignocellulosic biomass.

It is yet another aim of the present invention to provide food manufacturers such as millers, nut and seed processors, and the like, with a new value-added use for their agricultural waste products such as nut shells, seed hulls, corn cobs, etc.

These and other objects, aims, and advantages are realized by the present invention, which utilizes continuous extrusion reaction technology and high-pressure steam injection to chemically and physically modify lignocellulosic biomass to yield a wide variety of useful end products.

One of the many advantages of the present invention is that it does not require the use of hydrogen peroxide. Moreover, the delignification process described herein is continuous, rapid, and energy efficient.

The present invention includes a process for continuously treating lignocellulosic biomass which consists essentially of reacting the lignocellulosic biomass in a reaction medium including an aqueous solution of about pH 10.5 to 12.5 to yield an alkaline slurry, and then continuously feeding the slurry so formed into an extruder reactor at a temperature between about 150° F. and 350° F. High pressure steam is injected into the extruder reactor at a pressure of from about 50 pounds per square inch to 250 pounds per square inch. The slurry is then extruded to form an extrudate which is then disaggregated and dried to yield a modified lignocellulosic material. The lignocellulosic product so formed is highly lipophilic, and finds a wide variety of used, including as a composite flier.

The lignocellulosic product of the present invention, being highly lipophilic, is an excellent industrial absorbent, and finds use in the cleanup of spills of hydrophobic materials. For instance, the lignocellulosic product absorbs more than six times its own weight in fuel oil. This product therefore finds use in the cleanup of oil and gasoline spills, as well as for incorporation into absorbent spill dams, and the like.

The present invention also includes a further process for continuously treating lignocellulosic biomass which comprises reacting the lignocellulosic biomass in a reaction medium including an aqueous solution of about pH 10.5 to 12.5 to yield an alkaline wet mix, and continuously feeding the mix into an extruder reactor at a temperature between about 150° F. and 350° F., along with injecting stem into the extruder reactor at a pressure of from about 50 pounds per square inch to 250 pounds per square inch. The mix is then extruded to form a lignocellulosic extrudate which, rather than being dried, is immediately hydrolyzed to yield a liquid fraction containing soluble lignin and hemicellulose, and a solid fraction of reduced-lignin content cellulosic material. The liquid fraction is then separated from the solid fraction.

These and other advantages of the present invention will become clear upon a complete reading of the Detailed Description of the Invention, and attached claims.

DETAILED DESCRIPTION OF THE INVENTION

Figure 1:
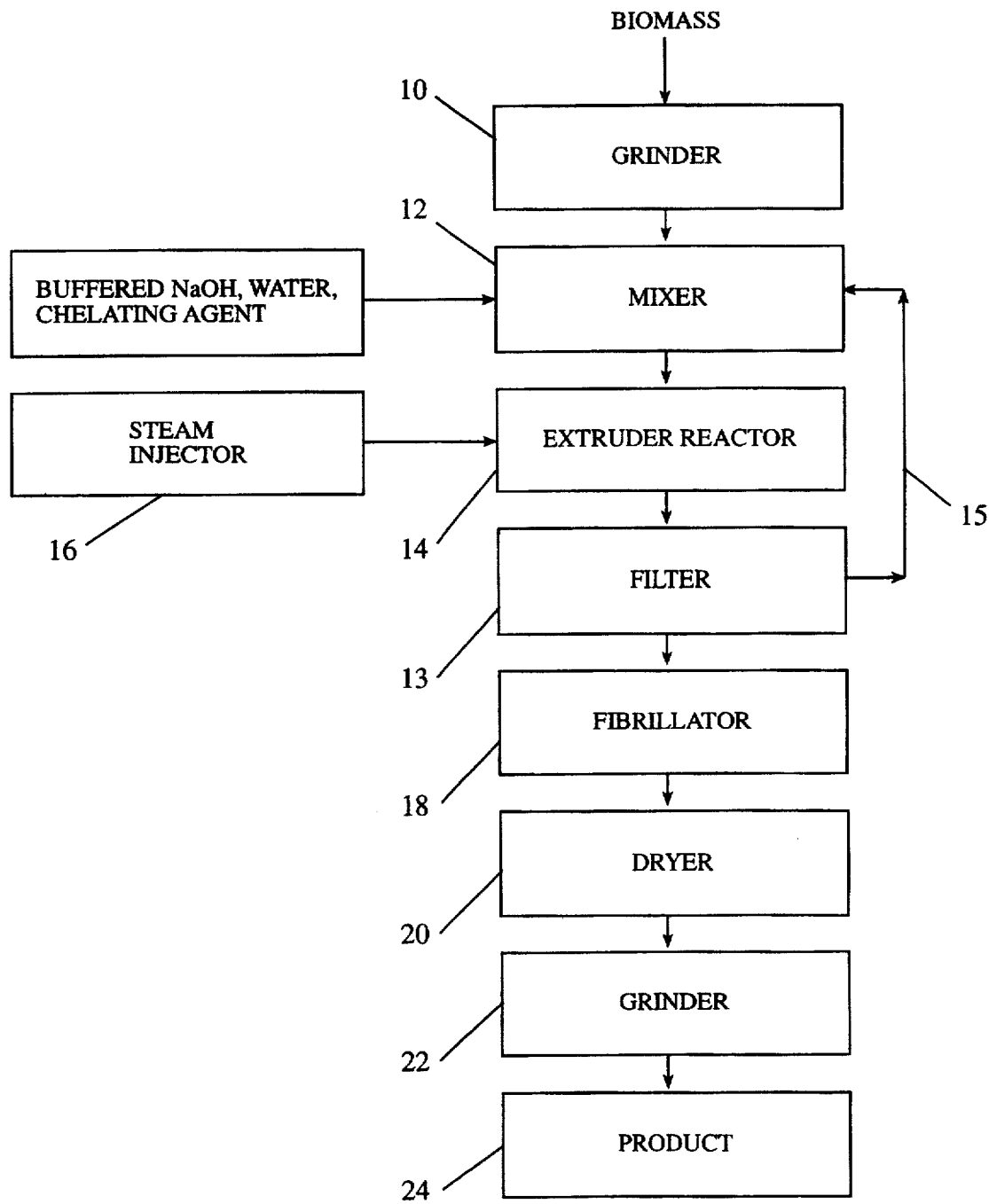
FIG. 1 is a schematic representation of a first embodiment of the process according to the present invention.

In the present invention, woody biomass, non-woody biomass, and combinations thereof are first solubilized in an aqueous alkaline solution with the optional addition of chelating agents. For purposes of the present invention, the term "non-woody" is meant to include organic plant material comprising no more than about 20% lignin. The term "woody" encompasses all other wood-like lignocellulose biomass materials. Additionally, as used herein, the terms "lignocellulosic substrate" or "biomass" mean any woody or non-woody plant materials from any source. This solution functions to make the biomass starting materials suitably pliant for the subsequent extrusion step. The alkalinity of the solution, generally from about pH 10.5 to pH 12.5, also results in alkaline hydrolysis of hemicellulose at pH's above 11.8.

The wet, now-alkaline biomass starting materials are then forced into a steam-jacketed extruder reactor into which is injected high-pressure steam. The high-pressure steam is injected directly into the extruder barrel, where it raises the temperature and the pressure within the extruder. The solubilized biomass starting materials are then extruded along with the injected high pressure steam. The high pressure, temperature, alkalinity, and mechanical shear within the extruder reactor modify the linkages between the lignins in the biomass and the cellulosic portions of the biomass. The lignin and hemicellulose within the biomass is altered by the treatment so as to become solubilizable. If desired, a large fraction of the lignin and hemicellulose within the treated biomass can be easily solubilized and separated from the insoluble cellulosic fibers after the mass emerges from the extruder reactor.

The modification reaction is generally quite rapid, with residence time within extruder ranging anywhere between about 20 seconds and 5 minutes. The reaction takes place in the absence of hydrogen peroxide, and generally (and preferably) in the absence of any other modifiers. However, conventional processing modifiers such as lubricants, pH modifiers, water, and the like may added to the reaction mixture as is generally known in the art.

After exiting the extruder, the resultant biomass product can be subject to one of two embodiments of the present invention.

In the first embodiment, the extrudate, which contains approximately 36% moisture and resembles wet cattle feed, is first fibrillated using a rotary-type drum dryer or similar device which contains internal paddles to physically disaggregate and fibrillate the lignocellulosic fibers. As it exits the extruder, the extrudate has a tendency to clump, which inhibits the final drying of the extrudate and the formation of individual fiber strands. Fibrillation results in the individual fibers being separated and "fractured" to resemble fine, hair-like fibers.

The fibrillated lignocellulose fibers are then thoroughly dried. Upon drying, the lignocellulosic fibers appear as very fine hair-like structures having a roughly uniform length of approximately one centimeter. The lignocellulosic fibers are very hydrophobic, and are readily compatible with all commonly-used extrudable plastics, including polyolefins, polystyrenes, acrylonitrile-butadiene-styrene copolymers, as well as other copolymer blends. When extruded with polyolefins, the resultant product is an excellent wood substitute.

In the first embodiment of the present invention, this hydrophobic, highly lipophilic, hair-like lignocellulosic fiber is the final product of the process. The fibers contain both modified cellulose and lignin, and find use as plastic fillers and modifiers. When added to polyolefins in an mount of from 40 to 60% by weight, the resultant product (either extruded or compression or injection molded) is an excellent wood substitute, having excellent strength, high modulus of elasticity, weather resistance, and termite resistance.

The lipophilic product is generally alkaline, having a pH in water on the order of 10.2. The alkalinity of the product is a benefit in that it allows extended storage of the product without worry of worm and other infestations. The high alkalinity of the lignocellulosic product prevents most common animal infestation. As a consequence, the lignocellulosic product can be stored cheaply without the need for extensive protection from common pests.

While not wishing to be held to any particular theory of operation, it is believed that upon extrusion of this lignocellulose fiber within a polyolefin or other plastic resin, the high heat of the extrusion process causes the lignins within the fibers to function in much the same way as they do in nature, binding the cellulose and the polyolefin matrix together to yield an extremely durable finished article.

In the second embodiment of the present invention, the extrudate is further processed to yield a predominately cellulose-containing solid product, and a lignin and hemicellulose-containing soluble fraction which can be utilized to produce feedstock chemicals such as ethanol, or sweeteners such as dextrose and xylose.

In the second embodiment of the present invention, the extrudate from the extrusion reactor is placed directly into an agitated warm-water hydrolyzing bath, or counter-current extraction column. It has been found that the lignins present within the extrudate have become largely solubilizable by the reaction within the extruder, and can be easily separated from the cellulose by mixing in warm or hot water for 10 to 30 minutes. This treatment removes approximately 80% of the lignin from the extrudate, as well as about 50% of any hemicellulose present in the extrudate. Comparison of the fibrillated and dried extrudate formed by the first embodiment of the present invention with the dried hydrolyzed product of the second embodiment reveals that hydrolysis results in a weight reduction of approximately 32%. This is a far greater solubilization of lignins than has been achieved in known prior art processes.

After the initial hydrolysis, the soluble fraction and the solids are separated (a Freeman press can be used), and the liquids may be subjected to enzymatic degradation, followed by fermentation to yield simple sugars such as xylose and glucose (glucan/xylan). The solid fraction is washed with fresh water and pressed one or more times with additional water, the washings being added to the soluble fraction from the initial hydrolysis.

The combined soluble fractions can be further chemically and enzymatically manipulated, as by enzymatic degradation followed by fermentation, to yield a number of fundamental feedstock chemicals including ethanol, butadiene, acetic acid, lactic acid, and the like. The feedstock chemicals so produced can be separated by distillation and other means whereby a renewable source of basic chemicals is realized.

The solids generated in the second embodiment of the present invention make excellent alkaline cellulose pulps for the paper industry. The cellulose fibers are usually dried, optionally comminuted to a desired mesh, and packaged in bales or bags. The alkaline cellulose pulp produced according to the present invention is capable of absorbing up to 30% w/w calcium carbonate, which is about twice the absorption of conventional acid-processed fibers.

Additionally, after neutralization, the cellulosic product is also fit for consumption, and can be incorporated into ruminant livestock foodstuffs as an excellent source of dietary fiber. This product is especially important as a feed additive in areas where cheap animal feed is not available. For instance, in many tropical areas, such as Hawaii, grain crops are not grown, and therefore very little cattle farming is done due to the high expense of feed. This, in turn, raises beef prices. However, the present product can be produced using such biomass as pineapple tops and sugar cane fodder, thereby providing tropical ranchers a source of cheap feed for their ruminant animals.

The cellulose fibers isolated by the second embodiment also find use as general purpose absorbents for such applications as diapers and catamenial devices, as well as for industrial applications; and also can be used in any application where fibrous or particulate material is needed, including the manufacture of fiber boards and insulation, as well as in composite molding, injection molding, extrusion, pultrusion, and the like.

The process of the present invention is directed to a continuous treatment of woody and non-woody biomass to produce hydrophobic lignocellulosic fiber, dietary cellulosic fiber, and other desirable cellulosic products in a convenient, rapid, and energy efficient manner. Additionally, the present process can be used to form chemical feedstocks for the production of organic chemicals such as ethanol, butadiene, acetic acid, lactic acid, and the like.

By using a steam-pressurized extruder reactor, lignocellulosic biomass can be conveniently converted via the process described herein into the desired product(s) in a fast and energy efficient manner, while substantially reducing the amount of chemicals needed to modify the biomass.

Because the process utilizes no harsh, toxin-forming acids, and further because only steam is generally injected into the extruder reactor, the resulting cellulosic material can be readily and easily processed using enzymes or yeast. The entire process being free of unneeded chemicals, enzymatic manipulation is not inhibited by processing acids which may poison yeasts or inactivate enzymes. Additionally, no furfural is produced.

An illustrative list of plant materials which can serve as starting materials for the present process includes tree fruits, such as apples, apricots, cherries, peaches, pears, and plums; citrus fruits such as lemon, lime, oranges and grapefruits; and bushberries such as blackberries, raspberries, strawberries, and blueberries. Further, cereal grains such as barley, make, oats, rice, rye, and wheat, as well as the waste material left after the processing of these materials, can be used in the claimed process. Agricultural residues such as wheat straw, rice straw, prairie grass, switch grass, and kenaf; hulls of grains and brans, such as oat hulls, wheat bran, soy hulls, sunflower hulls, rice hulls, barley stalks, maize stalks, make hulls, maize husks and silk, and make cobs; nut shells, including peanut hulls, pecan hulls, almond hulls and the like; beet pulp, pineapple tops, sugar cane, bagasse, newsprint, cardboard, etc., are also within the scope of the lignocellulosic biomass which can be utilized in the present invention, as are wood chips, bark, branches, yard waste, felled lumber, leaves, saw dust, and the like.

Reference is now made to FIG. 1 which illustrates in schematic form a first embodiment of the present invention.

First, the biomass staffing material is preferably chopped or reduced in size to roughly uniform particles not more than about two centimeters in length in grinder 10. The grinder may be of any conventional design normally used to comminute lignocellulosic material. The ground biomass is then fed to a mixer 12. At this point, an aqueous buffered alkali solution is added to the biomass in the mixer 12. The alkali solution functions to soften and solubilize the biomass, as well as to breakdown some of the cellulose and lignin linkages due to alkaline hydrolysis. Like the grinder, the mixer 12 may be of any conventional design, such as a ribbon mixer.

The buffered alkali solution preferably contains sodium hydroxide (NaOH) at a pH between about pH 10.5 and pH 12.5, and is heated to a temperature between about 80° and 120° F. Although NaOH is the preferred alkali, any suitably strong base, such as potassium hydroxide (KOH) will suffice. In some cases it may be preferred to keep the levels of sodium reduced, as in food grade applications. If this is the case, sodium levels in the finished food product can be minimized by the use of KOH rather than NaOH.

If hemicellulose within the biomass is to be retained within the solids, the pH of the solution should be adjusted to fall between about pH 11.4 and pH 11.8. Above about pH 11.8, hemicellulose contained within the biomass will be degraded by alkaline hydrolysis and be solubilized.

The biomass substrate is preferably allowed to remain in the mixer 12 for a period of at least 20 minutes at a temperature of between 80° F. and 120° F. This time and temperature profile has been shown to be effective to produce sufficiently softened and solubilized biomass within a reasonably short span of time. If desired, the temperature of the reaction medium may be reduced to ambient temperature to minimize the amount of energy consumed in this step; however, the reaction time will be correspondingly increased.

As noted above, the mixer 12 can be of any conventional design, such as a ribbon mixer, an agitator tank, a rotary mixer, a paddle mixer, and the like.

Optionally, a chelating agent may be added to the alkali solution within mixer 12. The chelating agent reacts and sequesters metal ions present within the biomass to prevent or diminish the formation of precipitates. A sufficient amount, preferably from about 2.5% and 4.0% v/v of a chelating agent, such as a sodium silicate, EDTA, or VERSENEX 80-100 (Dow Chemicals) which is effective to chelate the metal ions in the solution, is added to the mixer 12. The addition of a chelating agent aids in preventing unwanted precipitation of insolubles such as metals or alkali-insoluble metal hydroxides. These precipitates tend to form deposits on the downstream components of the apparatus used in the present invention, thereby fouling their operation. Additionally, the chelating agent coats metal surfaces within the downstream extruder barrel, thereby preventing product burn-on or buildup on the machine surfaces.

The biomass is then passed to an extruder reactor 14. At the time of introduction to the extruder reactor 14, the biomass will generally contain about 20 to 65% moisture by weight, and in most circumstances approximately 40% moisture by weight.

After introduction of the biomass, a steam injector 16 injects pressurized steam into the extruder barrel. The steam should be injected at about 50 pounds per square inch (psi) to about 250 psi. Steam injection at about 150 to 200 psi is preferred. The extruder reactor 14 allows for the effective treatment of the substrate with high-pressure steam at higher solids levels than steam treatment in a pressure cooker. The extruder eliminates a substantial amount of the liquid stream and improves the recovery of carbohydrate products as in the case of animal feeds. Moreover, the friction and pressure generated within the extruder reactor 14 accelerates the reaction and reduces the amount of steam needed to modify the lignocellulosic linkages with the biomass. As noted above, the mix generally enters the extruder reactor 14 at approximately 40% moisture. At that moisture level, the extrudate generally exits the extruder reactor 14 having a moisture content of about 36 to 40%. In general, the extrudate leaving the extruder reactor will have a moisture content slightly less than the incoming biomass mix.

Upon introduction into the extruder 14, the pH of the substrate is preferably at a level between about pH 11.2 and about pH 12.2, more preferably still between pH 11.4 and pH 11.8. Ideally, the extruder reactor will process approximately 4,000 lbs. of substrate per hour continuously. The advantage of using of an extruder reactor is that it replaces steam cooking in a batch process with a continuous process, thereby making the entire process much faster, more efficient, and more consistent.

The extruder reactor 14 is of conventional design, normally manufactured from stainless steel or other non-corrosive material. The extruder reactor may be a single or a twin-screw extruder. Preferably, the extruder reactor 14 is a single-screw stainless steel extruder with a steam jacket, and which is capable of food-grade operation. Preferred commercially-available extruder reactors for purposes of the present invention include the EXTRUDECK Model 925 line of steam jacketed continuous extrusion cookers with cram feeders. These extruders are rated from 200 to 250 horsepower for high capacity industrial applications. These extruders also include a cram feeder device which provides a uniform and controllable feed rate to the extruder.

The preferred extruder reactor 14 includes a single screw stainless steel barrel approximately 10 to 16 inches in diameter, and 6 to 8 feet in length. The extruder barrel should be made of a high-carbon alloy or stainless steel, and have sufficient mechanical strength to withstand pressures exceeding 700 psi and temperatures exceeding 350° F.

A typical power source for such an extruder is a 200 horsepower, 3-phase electric motor. A gear reducer is generally employed to reduce the 1800 RPM electric drive to about a 300 RPM extruder speed. Preferably, a cram feeder hopper powered by a variable-speed motor feeds the biomass material into the throat of the extruder barrel.

The extruder reactor 14 itself may be divided into as many as eight sections, each section being separated by a stem lock. In the first section, a cram feeder is designed to grab and feed the biomass material into the first compression zone. Preferably, this first section operates at a speed of about 300 RPM with a single screw butting against a shear block to pressurize the section. The final section of the extruder is an ancular die which extends 5 to 10 centimeters past the last steam lock.

It is preferred that remotely located safety sensing devices register both temperature and pressure along the length of the extruder reactor 14. Both manual and automatic shutdown devices should be located throughout the system. As a safety measure, a shroud, generally formed of stainless steel, should surround the extruder. The shroud includes devices which continuously monitor the toxicity level of any emitted vapors. This important safety aspect of the system is able to signal danger and/or shut down the apparatus while simultaneously venting the vapors to an exhaust system until the toxicity level is brought under control.

The steam injector 16 can be of any conventional design, such as a series of port inlets. The steam injector functions to inject high-pressure steam into the extruder barrel.

As noted above, it is preferred that the steam be injected into the extruder 14 at a pressure of approximately 150 psi. The total pressure within the extruder barrel itself (including the pressure due to the injected steam) should range between approximately 270 and 450 psi.

The temperature within the extruder reactor 14 should be maintained within the range of from about 260° to 325° F., and preferably between 265° and 290° F. This is done by means of a steam jacket. At higher temperatures, the biomass may scorch. At lower temperatures, the workability of the biomass is adversely affected.

At these pressures and temperatures, the delignification/modification reaction within the biomass takes place quite rapidly, normally within approximately 1.5 to 5 minutes.

Monitoring gauges are strategically placed along the length of the extruder 14 to indicate the pressure, temperature, and pH of the biomass substrate as it moves through the extruder. The extruder barrel may also include ports for the injection of additional chelating agents, alkaline reagents, water, or other extrudate modifiers.

As noted above, if hemicellulose is to be retained within the solids, the pH within the extruder 14 should be maintained between about 11.2 and 11.8. If the pH exceeds 11.8, rapid degradation of the hemicellulose via alkaline hydrolysis will occur. Hemicellulose retention is optimized by maintaining the pH within the extruder to about pH 11.4. Adjustments can be made in the pH of the biomass within the extruder reactor 14 by injection of suitable buffered solutions into the extruder barrel. Preferably, these pH adjustments are controlled by an automatic, computer-controlled injection system.

It is a substantial benefit of the present invention that the use of hydrogen peroxide to modify the biomass has been eliminated. The reasons for this are several. First, the cost of chemicals needed to produce the products described herein are significantly reduced. Eliminating the use of hydrogen peroxide realizes a cost savings of approximately $10 to $13 dollars per ton of modified biomass processed.

Second, pressurized steam is widely used in many industry applications, and apparatus to generate, handle, and utilize pressurized steam is readily available in the market.

Third, because no hydrogen peroxide is introduced into the biomass, there is no worry about having to remove hydrogen peroxide from the finished product. This is an especially important concern if the cellulose product is to be utilized as a food supplement. Because hydrogen peroxide is entirely absent from the present process, the likelihood of a food-grade cellulose product formed using the described process being granted Generally Regarded As Safe (GRAS) certification by the Food and Drug Administration is greatly increased.

Fourth, no chemicals are introduced into the lignocellulosic material which may adversely affect subsequent enzymatic or biological manipulations.

The biomass leaving the extruder 14 should generally have a moisture level between approximately 30 and 40%, and preferably about 36% moisture. The temperature of the biomass at this point is generally in the range of from 195° to 200° F. Additionally, the pH of the biomass as it exits the extruder is normally about pH 10.2. Of course, the final pH of the extrudate will vary depending largely upon the pH of the initial alkaline solution used to solubilize the biomass starting materials. The other parameters, such as moisture content and temperature will depend largely on the nature of the starting biomass reactants.

In the first embodiment of the present invention, upon exiting the extruder reactor 14, the substrate is passed through filter 13. The filter 13 may be any of a number of conventional filter designs known in the art for removing a reaction medium from a substrate. The function of the filter is the critical concern, rather than the design of the filter. A preferred filter is a vibrating screen filter. The purpose of the filter 13 is to remove the alkali solution from the reacted biomass and return it to the mixer 12 via recirculation line 15.

Return of the alkali solution to the mixer 12 increases the overall efficiency and cost profile of the present process. If necessary, the solution which is recycled back to the mixer 12 may be pH corrected by the addition of new alkali. Additionally, it may be necessary to correct the temperature of the recycled solution to be within the preferred 80° to 120° F. temperature range prior to re-introducing the solution into the mixer 12. The alkali solution may be continuously recycled back into the mixer 12 through recirculation line 15 until the solution loses its solubilizing ability. The contaminated reaction medium is then replaced with a fresh medium.

The filtered biomass is then transferred to a fibrillator 18. The fibrillator 18 functions to partially dry, disaggregate, de-clump, and dissociate the individual fibers of the biomass extrudate into individual fibers. The fibrillator physically and strenuously agitates the biomass extrudate to cause physical separation of the individual lignocellulosic strands of the extrudate.

The fibrillator 18 is preferably a rotary drum-type dryer which includes internal paddles to disaggregate the biomass extrudate. A heat source may also be incorporated into the fibrillator 18 to partially dry the biomass extrudate. Alternative devices, such as high-power agitators, for instance conveyor agitators, ball mills, and the like, can also be used to fibrillate the biomass extrudate. A closed system is preferred because it reduces dust formation.

After being fibrillated, the lignocellulosic extrudate appears as "fractured," hair-like strands of roughly uniform dimensions.

These hair-like lignocellulosic structures are then transferred to a dryer 20 where they are dried to a moisture content of about 36%, to yield a final lignocellulose product 24. The dryer 20 can be of any conventional design which is capable of drying the fibrillated lignocellulosic product. The dryer 20 may also include additional agitation to further fibrillate the lignocellulosic product.

The lignocellulosic product 24 is lipophilic, and generally alkaline, having a pH of around 10 upon complete drying.

The product 24 is highly compatible with a wide variety of plastic compositions, and finds use as a composite filler and stiffener. The cellulose product 24 can be incorporated into a wide range of composite materials which exhibit excellent strength, modulus, and weather-resistant characteristics. Such composite materials make excellent wood substitutes. The cellulose product 24 is compatible with all commonly utilized synthetic resins, including polyolefins such as polyethylenes (including HDPE, LDPE, and LLDPE), polypropylene, polybutylene, etc.; polystyrene and modified polystyrenes (e.g. polymethylstyrene, polyethylstyrene), polyethylene terephthalates, ABS, thermoplastic polyesters, co-polymers, and the like. It is compatible with extrusion and pultrusion technologies, as well as injection and compression molding.

½-inch thick sheets have been extruded from 40–60, 50–50, and 60–40 weight percent mixtures of the product 24 and polyethylene, respectively. The sheets can be sanded, sawed, nailed, and generally worked just as natural wood.

In addition to sheets, when incorporated into polyethylene in proportions ranging from 40 to 60% by weight, the cellulose product 24 yields a composite material which can be extruded into rods, blocks, tubes, and shapes of any desired cross-sectional profile. The composite material so formed can also be injection molded to create finished articles of any desired shape or size.

Of notable benefit, the high pH of the product 24 renders it resistant to most pests which infest cellulosic matter. Worms and the like, which must ordinarily be guarded against, cannot utilize the product 24 as a food source due to its high alkalinity. This makes long-term storage of the product less costly, with less waste.

The cellulose product 24 can also be used alone for such uses as kitty litter or as an industrial lipophilic absorbent. After thorough drying, the product 24 may be baled or bagged for delivery and storage.

Figure 2:
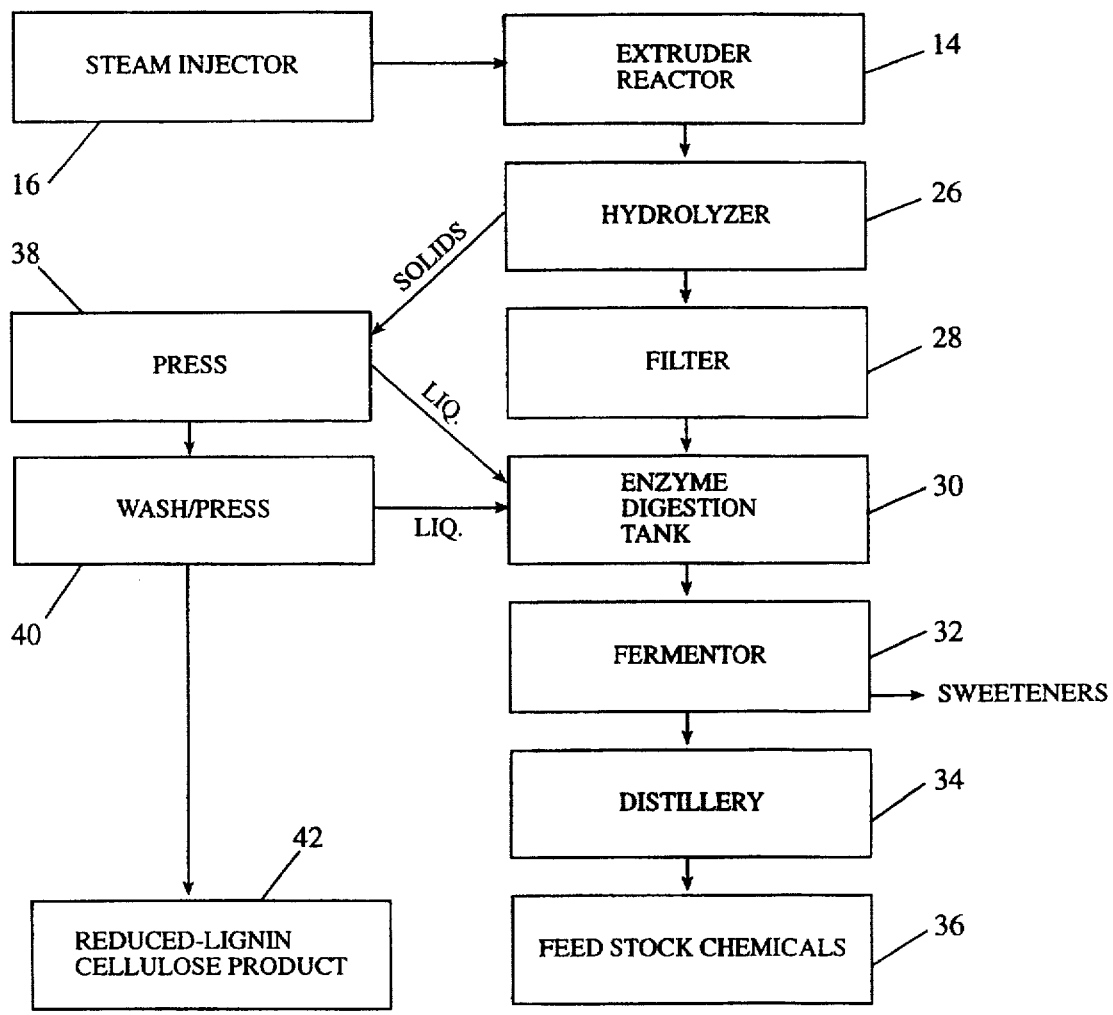
FIG. 2 is a schematic representation of a second embodiment of the process according to the present invention.

In a second embodiment of the present invention, which is illustrated schematically in FIG. 2, the extrudate exiting the extruder, rather than being fibrillated and dried, is placed immediately into a hydrolyzer 26. The hydrolyzer 26 is preferably an agitated water tank having a temperature of at least 140° F., and more preferably still a counter-current continuous extractor. The hydrolyzer functions to remove hemicellulose and lignins from the extrudate.

After vigorous washing in the hydrolyzer 26, the wet mass is then transferred to filter 28 where the liquid-borne solubles are separated from the solids. Here, the filter 28 can be any type of device for separating liquids and solids. The filter may also be a compound device, such a screen device in combination with a press 38 to further remove water entrained within the extrudate. The solids from the press 38 may be washed and again pressed 40 to further remove any solubles still remaining within the solid matrix. This washing and filtering/pressing step may optionally be repeated, as shown schematically at reference number 40 in FIG. 2. This step may be repeated as often as deemed necessary.

After washing and pressing, the solid product is a reduced-lignin cellulose product 42. The dried product 42 is, on average, about 32% reduced in mass from the dried mass of an equal portion of the extrudate as it exits extruder reactor 14. This 32% weight reduction is due to the removal of hemicellulose and lignins from the extrudate by the hydrolyzing and pressing steps described above.

After being thoroughly dried, the reduced-lignin cellulose product 42 may be baled or bagged for delivery to end-users.

The reduced-lignin product 42 is suitable for a broad range of food and non-food uses. For instance, the product 42 is suitable, as is, for animal consumption as dietary fiber. The intermediate washing steps results in a product composed largely of cellulose at a neutral pH.

The product 42 also makes an excellent biodegradable packing material. It is sufficiently rigid and structurally sound to provide stable support, resiliency, and cushioning, while sufficiently light so as not to add undue weight to large shipments.

The reduced-lignin product 42 preferably has a particle size small enough to pass through a 100 mesh screen. The product can be comminuted to such a desired size by any conventional method. As note above, the reduced-lignin product is acceptable as a food grade material for a total dietary fiber. It also complies with the current FDA residue requirements, therefore rendering it suitable for a Generally Regarded As Safe (GRAS) designation.

The liquid fraction from filter 28 is transferred to enzyme digestion tank 30. In tank 30, the liquid fractions from filtration and pressing may be enzymatically digested to yield basic chemicals normally considered feedstock chemicals. For instance, sweeteners can be produced by the addition of appropriate fungal cellulose enzyme complexes, such as *Trichoderma reesei*, to the tank 30. This microorganism is native to the digestive system of many ruminant species. This enzyme, as well as others (such as hemicellulases), catalyzes conversions of the cellulose and hemicellulose within the liquid fractions which lead to the ultimate formation of sugars such as xylose and glucose (xylan/glucan).

After digestion, the digested mass is be transferred to fermentor 32. Subsequent reactions within the fermentor 32 result in the formation of various sweeteners which have commercial value in and of themselves. These sweeteners may be isolated and marketed as final products of the subject process, and shown schematically in FIG. 2.

Alternatively, fermentation may be allowed to proceed further in order to break down the sugars to form such products as ethanol, acetic acid, butanol and other chemical derivatives. This can be accomplished utilizing any number of yeast strains or other microbes. Commonly used yeasts for fermentation include various strains of *Saccharomyces cerevisiae*, *P. stipitus*, and *Kluyveromyces marxianus*. The particular yeast is chosen on the basis of the chemical transformation which it metabolizes, and the parameters under which the microbe thrives (e.g. optimum temperature, acidity, etc.). The mixed mass of chemicals is transferred to distillery 34 for separation of the components of the mass into useable feed stock chemicals 36.

The entire system used to practice the present process may be automatically controlled to maintain pre-determined pressures, temperatures and retention times, depending upon the substrate used, the amount of water used, and the amount of modification desired, The whole system can be computerized and triggered to respond to pressures, temperatures, or end results, and the capacity desired.

The apparatus may be powered by diesel engine. Coolant water circulated through the engine block of the diesel power plant can be used as a heat source to generate steam for high pressure injection, and to provide heat to cook the biomass within the extruder. Excess hot water is recycled to the heat the initial mixer 12, and then transferred back to the diesel motor block to cool the engine.

It is within the scope of the present invention to customize the apparatus to leave in more lignin and hemicellulose or take out more by simply changing the pH level during the process. Additionally, the process may be mobilized as a portable unit, which would effect tremendous savings on the cost of transporting the substrate for livestock feeding.

The following examples are given to illustrate certain preferred embodiments of the process of the present invention. The examples are for illustrative purposes only, and are understood not to limit the invention claimed herein in any fashion.

EXAMPLES

Example 1: Material and Energy Balance for the Process

Here, an experiment was run to measure the energy and mass input, and the mass output of the present invention as it might be practiced on an industrial scale. One ton per hour of shredded biomass (dry basis) is fed to a ribbon blender/ cram feeder, where the biomass is mixed with 60 to 180 pounds of alkali solution (50% NaOH). The wetted, alkali biomass is then fed to an extruder. Pressurized steam (150 psi) is injected into the extruder barrel at a point near the biomass feed point.

The biomass is then extruded at a temperature of from 260° to 325° F. The extruder was powered by a 250 HP electric motor, drawing 125 amps, for a net energy input of 172 KW.

The extruded biomass is then extracted in a countercurrent extraction column with hot water. 2,500 liters/hour of water is heated (in a heat exchanger contacting the extracted xylan/glucan/lignin liquid stream) and contacted with the combined biomass and liquids from a Freeman press to extract the solubilized lignin and xylan/glucan.

Two streams leave the process: a pressed cellulose stream of approximately 50% solids (40% cellulose at 890 kg/hr), and a liquid xylan/glucan/lignin stream (2,800 liters/hr, 75 g/l lignin, 60 g/l xylan/glucan).

The total energy consumed per ton of biomass is approximately 200 KW of electrical energy, 83 kg of steam, and approximately 70 kg of 50% NaOH solution.

Example 2: Solubilization of Lignin and Hemicellulose

This example illustrates the effectiveness of the present process for solubilizing the lignin and hemicellulose within biomass. Here, straw was treated in the same fashion as described in Example 1. However, after extrusion and prior to hydrolysis, a first 50 g portion of the extrudate was weighed immediately upon exiting the extruder, then dried and weighed again. A second 50 g portion of the extrudate was hydrolysed and the percentage of soluble solids determined.

Comparative samples were run using the hydrogen peroxide injection process described in U.S. Pat. No. 5,023,097, to Tyson, which describes a biomass extrusion process which utilizes hydrogen peroxide to effect solubilization. The results are shown in Table 1. In Table 1, the first three samples (Corn Stalks, Switch Grass, and Wheat Straw) were processed using the hydrogen peroxide treatment described in the '097 patent. The fourth sample (Wheat Straw II), was processed using the presently described process. As can be seen from the table, the present process resulted in over 32% of the solids being solubilized. This is more than twice the amount of solubilization achieved with the hydrogen peroxide process.

TABLE 1

| | Corn Stalks | Switch Grass | Wheat Straw | Wheat Straw II |
|---|---|---|---|---|
| Dry solids/50 g | 20.5 g | 28.3 g | 44.1 g | 44.9 g |
| Soluble solids after treatment | 2.52 g | 4.4 g | 6.6 g | 14.5 g |
| % Soluble solids | 12.20% | 15.60% | 14.90% | 32.30% |

Example 3: Enzymatic Treatment with Hemicellulase

In this Example, the enzymatic hydrolysis of the Wheat Straw II product described in Example 2 was performed. Here, as described in Example 1, the biomass was separated into two streams, a solid, cellulose stream, and a liquid stream of the dissolved solubles (lignins and hemicellulose).

The liquid stream was treated, with gentle heating, with the enzyme hemicellulase. Upon treatment, the xylose concentration rose from an initial 5.3 g/l to a final concentration of 6.8 g/l in 3 hours.

The solid cellulose stream was also treated in an analogous fashion. The solid fraction yielded a 68% yield of the cellulose to sugars after 12 hours, along with a large release of xylose (initial concentration 2 g/l, final concentration (after 12 hrs) 8 g/l). The formation of xylose indicates that the recovery of lignin and xylan/glucan in the liquid extraction was not complete. A mass balance of the xylose produced in the enzymatic reaction of the solid portion indicates that approximately 48% of the hemicellulose within the biomass sample was solubilized by the treatment.

Based on these yields, the present process could be coupled with a two-stage fermentation process to produce ethanol from biomass in an efficient and economically viable fashion. For instance, the solubilized stream is fermented using a "xylose to ethanol" yeast, while the cellulose is fermented using either a thermo-tolerant, "glucose to ethanol" yeast and/or bacteria in an SSF-type reactor (simultaneous saccharification and fermentation).

The present invention is not limited to the embodiments and examples listed above, but includes all such forms, modifications, and variations thereof as are encompassed by the following claims.

What is claimed is:

1. A process for continuously treating lignocellulosic biomass consisting essentially of:
   a. reacting the lignocellulosic biomass in a reaction medium including an aqueous solution of about pH 10.5 to 12.5 to yield an alkaline mix;
   b. continuously feeding the mix of step a) into an extruder reactor at a temperature between about 150° F. and 350° F.;
   c. injecting steam into the extruder reactor at a pressure of from about 50 pounds per square inch to 250 pounds per square inch;
   d. extruding the mix of step a) in the absence of hydrogen peroxide to form an extrudate; and
   e. disaggregating and drying the extrudate to yield a modified lignocellulosic material.

2. The process of claim 1, wherein the lignocellulosic biomass is selected from the group consisting of oat hulls, wheat bran, soy hulls, sunflower hulls, rice hulls, barley, corn hulls, beet pulp, switch grass, wheat straw, kenaf, yard waste, peanut hulls, bark, corn cobs, rice straw, pineapple tops, sugar cane, bagasse, newsprint, cardboard, corn husks, agricultural residues, and combinations thereof.

3. The process of claim 1, wherein the lignocellulosic biomass is reduced in size to particles not more than ½ inch in length prior to reacting in the reaction medium.

4. The process of claim 1, wherein in step a) the pH of about 10.5 to about 12.5 is attained by adding an alkaline compound selected from the group consisting sodium hydroxide and potassium hydroxide to the reaction medium.

5. The process of claim 1, wherein in step d) the mix is extruded at a temperature of from about 260° to 325° F.

6. The process of claim 1, wherein in step c) the steam is injected into the extruder reactor at a pressure of from 150 to 250 pounds per square inch.

7. The process of claim 1, wherein in step c) the steam is injected into the extruder reactor at a pressure of about 150 to 200 pounds per square inch.

8. The process of claim 1, wherein in step d) the mix is extruded at a pH between about 11.2 and about 11.8.

9. The process of claim 1, wherein step a) further consists essentially of adding a chelating agent to the reaction medium in an amount sufficient to chelate metals present within the reaction medium.

10. The process of claim 9, wherein in step a) a chelating agent selected from the group consisting of sodium silicate and ethylenediamine tetraacetic acid, and mixtures thereof is added to the reaction medium.

11. The process according to claim 1, wherein step a) further consists essentially of adding buffering agents to the reaction medium.

12. The process according to claim 1, wherein the lignocellulosic biomass is selected from the group consisting of woody cellulosic substrates and non-woody cellulosic substrates.

* * * * *